United States Patent
Strassner

(10) Patent No.: US 12,048,434 B2
(45) Date of Patent: *Jul. 30, 2024

(54) SYSTEMS AND METHODS FOR SUTURE FAILURE DETECTION DURING SURGICAL STAPLING

(71) Applicant: Covidien LP, Mansfield, MA (US)

(72) Inventor: Haley E. Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,082

(22) Filed: Apr. 11, 2023

(65) Prior Publication Data
US 2023/0240684 A1      Aug. 3, 2023

Related U.S. Application Data

(63) Continuation of application No. 17/355,250, filed on Jun. 23, 2021, now Pat. No. 11,622,769.
(Continued)

(51) Int. Cl.
*A61B 17/115*      (2006.01)
*A61B 90/00*      (2016.01)
(Continued)

(52) U.S. Cl.
CPC .......... *A61B 17/1155* (2013.01); *A61B 90/06* (2016.02); *A61B 2017/00119* (2013.01);
(Continued)

(58) Field of Classification Search
CPC . A61B 17/1155; A61B 17/3403; A61B 90/06; G16H 40/63
See application file for complete search history.

(56) References Cited

U.S. PATENT DOCUMENTS

| | | | |
|---|---|---|---|
| 8,808,311 B2 * | 8/2014 | Heinrich | A61B 90/06 227/176.1 |
| 11,622,769 B2 * | 4/2023 | Strassner | A61B 90/06 227/179.1 |

(Continued)

FOREIGN PATENT DOCUMENTS

| | | |
|---|---|---|
| EP | 3412225 A1 | 12/2018 |
| WO | 2012112249 A1 | 8/2012 |
| WO | 2019133138 A1 | 7/2019 |

OTHER PUBLICATIONS

Extended European Search Report dated Jan. 4, 2022 corresponding to counterpart Patent Application EP 21187262.7.

*Primary Examiner* — Nathaniel C Chukwurah
(74) *Attorney, Agent, or Firm* — Carter, DeLuca & Farrell LLP

(57) ABSTRACT

A computer-implemented method for controlling a surgical stapling instrument for stapling tissue includes advancing an anvil assembly in relation to a staple cartridge to a first position defining a tissue gap between the staple cartridge and the anvil assembly and clamping tissue, the clamped tissue including a suture, measuring a first force of tissue compression of the tissue clamped within the tissue gap with the anvil assembly at a first time point, determining whether the measured first force is greater than a threshold, measuring a second force of tissue compression of the tissue clamped within the tissue gap at a second time point in response to the determination that the first force is greater than the threshold, determining whether the suture failed based on the measured second force being an amount less than the measured first force, and stopping the advancing of the anvil assembly based on the determined suture failure.

20 Claims, 7 Drawing Sheets

Related U.S. Application Data

(60) Provisional application No. 63/056,765, filed on Jul. 27, 2020.

(51) Int. Cl.
 *A61B 17/00* (2006.01)
 *A61B 17/11* (2006.01)

(52) U.S. Cl.
 CPC . *A61B 2017/1142* (2013.01); *A61B 2090/064* (2016.02); *A61B 2562/0261* (2013.01)

(56) References Cited

U.S. PATENT DOCUMENTS

| | | |
|---|---|---|
| 2012/0205419 A1 | 8/2012 | Weir et al. |
| 2018/0353186 A1 | 12/2018 | Mozdzierz et al. |
| 2019/0059884 A1 | 2/2019 | Shelton, IV et al. |
| 2019/0200997 A1 | 7/2019 | Shelton, IV et al. |
| 2019/0343517 A1 | 11/2019 | Zemlok et al. |
| 2020/0015820 A1 | 1/2020 | Contini et al. |

\* cited by examiner

SYSTEMS AND METHODS FOR SUTURE FAILURE DETECTION DURING SURGICAL STAPLING

CROSS-REFERENCE TO RELATED APPLICATIONS

The present application is a continuation of U.S. patent application Ser. No. 17/355,250, filed on Jun. 23, 2021, now U.S. Pat. No. 11,622,769, which claims the benefit of and priority to U.S. Provisional Patent Application Ser. No. 63/056,765, filed on Jul. 27, 2020. The entire disclosures of the foregoing applications are incorporated by reference herein.

FIELD

This disclosure relates generally to powered surgical stapling instruments, and more particularly, to a method for controlling surgical stapling instruments based upon detecting suture failure and to a surgical stapling instrument for performing the method.

BACKGROUND

Anastomosis is the surgical joining of separate hollow organ sections. Typically, an anastomosis procedure follows surgery in which a diseased or defective section of an organ is removed, and the remaining end sections of the organ are joined via a surgical stapling instrument. Depending on the desired anastomosis procedure, the remaining end sections may be joined by circular or side-to-side organ reconstruction methods, for instance.

In a circular anastomosis procedure, the remaining end sections of the organ are joined by means of a surgical stapling instrument which drives a circular array of staples through the remaining end sections and simultaneously cores any tissue interior of the driven circular array of staples to free a tubular passage within the organ. During a procedure, a purse-string suture may be tied around one or both sides of the surgical stapling instrument in order to enhance the integrity of the anastomosis and help prevent leakage. In some instances, due to either surgeon technique or tissue properties, the purse string can fail during clamping of tissue by the surgical stapling instrument. When the purse-string suture fails, an entire tissue donut may not be captured by the device and could leak, or an incomplete donut may be formed.

A continuing need exists for a stapling instrument that can determine when a purse-string suture fails during the clamping of tissue.

SUMMARY

In accordance with the disclosure, a computer-implemented method for controlling a surgical stapling instrument for stapling tissue includes advancing an anvil assembly in relation to a staple cartridge to a first position defining a tissue gap between the staple cartridge and the anvil assembly and clamping tissue therebetween, the clamped tissue including a suture therethrough, measuring a first force of tissue compression of the tissue clamped within the tissue gap with the anvil assembly at a first time point, determining whether the measured first force is greater than a predetermined threshold, measuring a second force of tissue compression of the tissue clamped within the tissue gap at a second time point in response to the determination that the first force is greater than the predetermined threshold, determining whether the suture failed based on the measured second force of tissue compression being a predetermined amount less than the measured first force of tissue compression, and stopping the advancing of the anvil assembly based on the determined suture failure.

In an aspect, the first force of tissue compression and the second force of tissue compression may be measured by a strain gauge.

In another aspect, determining whether the suture failed may be further based on a shape of a curve of a force applied to the clamped tissue over time.

In yet another aspect, the method may further include preventing staple firing when the second force of tissue compression is less than the first force of tissue compression.

In an aspect, the method may further include displaying a warning in response to the suture failure being determined.

In another aspect, the displayed warning may include at least one of a warning to inspect a surgical site or to unclamp the tissue.

In yet another aspect, the method may further include generating an audio warning when suture failure is determined.

In still yet another aspect, the predetermined threshold may be greater than a predetermined acceptable range of tissue compression.

In still yet another aspect, the method may further include determining a decrease in tissue clamping force between the first force of tissue compression and the second force of tissue compression.

In still yet another aspect, measuring the first force of tissue compression of the tissue clamped within the tissue gap with the anvil assembly at a first time point may include measuring the first force of tissue compression when the anvil assembly is not within a predetermined distance range of the staple cartridge.

In accordance with the disclosure, surgical stapling instrument includes an anvil assembly including an anvil head and an anvil center rod extending proximally from the anvil head, a reload assembly including an annular staple cartridge including a plurality of staples, a processor; and a memory. The memory includes instructions stored thereon, which when executed by the processor cause the surgical stapling instrument to advance the anvil assembly in relation to the staple cartridge to a first position defining a tissue gap between the staple cartridge and the anvil assembly and clamping tissue therebetween, the clamped tissue including a suture therethrough, measure a first force of tissue compression of the tissue clamped within the tissue gap with the anvil assembly at a first time point, determine whether the measured first force is greater than a predetermined threshold, measure a second force of tissue compression of the tissue clamped within the tissue gap at a second time point in response to the determination that the first force is greater than the predetermined threshold, determine whether the suture failed based on the measured second force of tissue compression being a predetermined amount less than the measured first force of tissue compression, and stop the advancing of the anvil assembly based on the determined suture failure.

In an aspect, the first force of tissue compression and the second force of tissue compression may be measured by a strain gauge.

In another aspect, determining whether the suture failed may be further based on a shape of a curve of a force applied to the clamped tissue over time.

In yet another aspect, the instructions, when executed by the processor, may further cause the surgical stapling instrument to prevent staple firing when the measured second force of tissue compression is less than the first force of tissue compression.

In still yet another aspect, the instructions, when executed by the processor, may further cause the surgical stapling instrument to a warning in response to the suture failure being determined.

In still yet another aspect, the displayed warning may include at least one of a warning to inspect the surgical site or to unclamp the tissue.

In still yet another aspect, the instructions, when executed by the processor, may further cause the surgical stapling instrument to generate an audio warning when suture failure is determined.

In still yet another aspect, the predetermined threshold may be greater than a predetermined acceptable range of tissue compression.

In another aspect, the instructions, when executed by the processor, may further cause the surgical stapling instrument to determine a decrease in tissue clamping force between the first force of tissue compression and the second force of tissue compression.

In accordance with the disclosure, a non-transitory computer-readable medium storing instructions which, when executed by a processor, cause the processor to perform a method for controlling a surgical stapling instrument, including advancing an anvil assembly in relation to a staple cartridge to a first position defining a tissue gap between the staple cartridge and the anvil assembly and clamping tissue therebetween, the clamped tissue including a suture therethrough, measuring a first force of tissue compression of the tissue clamped within the tissue gap with the anvil assembly at a first time point, determining whether the measured first force is greater than a predetermined threshold, measuring a second force of tissue compression of the tissue clamped within the tissue gap at a second time point in response to the determination that the first force is greater than the predetermined threshold, determining whether the suture failed based on the measured second force of tissue compression being a predetermined amount less than the measured first force of tissue compression, and stopping the advancing of the anvil assembly based on the determined suture failure.

BRIEF DESCRIPTION OF DRAWINGS

Systems and methods for controlling surgical stapling instruments for clamping and stapling to a force are disclosed herein with reference to the drawings, wherein.

DETAILED DESCRIPTION

Figure 1:
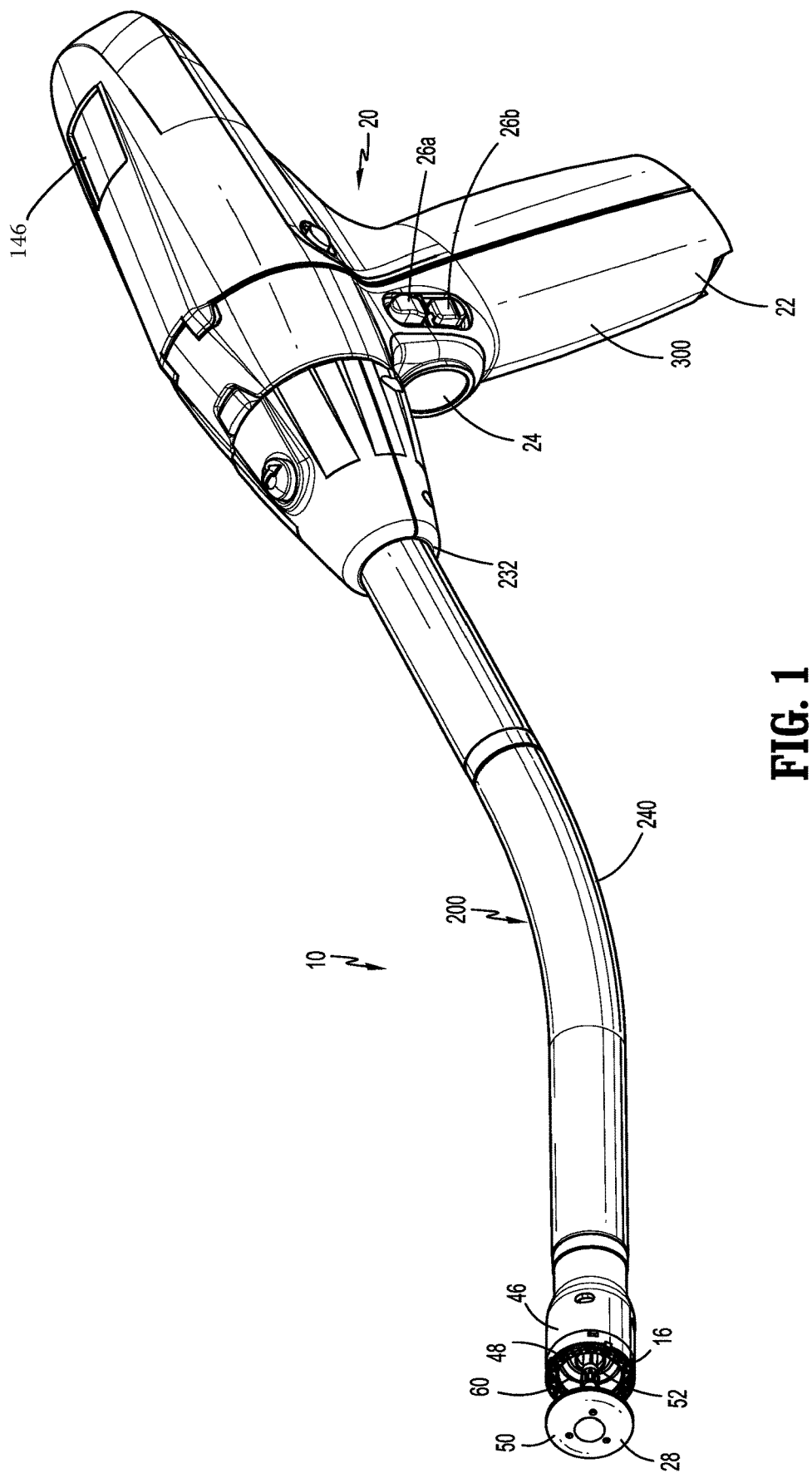
FIG. 1 is a perspective view of a surgical stapling instrument in accordance with the disclosure.

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

This disclosure is directed to a surgical stapling instrument that controls stapling of tissue based in part on distinguishing between staple formations that may prevent leaks and staple formations that are not sufficiently closed.

FIG. 1 illustrates a surgical stapling instrument shown generally as surgical stapling instrument 10. The surgical stapling instrument 10 is a circular stapling instrument and includes a handle assembly 20, an adapter assembly 100 that extends distally from the handle assembly 20, a reload assembly 16 that is supported on a distal portion of the adapter assembly 100, an anvil assembly 50 that is operatively coupled to the adapter assembly 100, and a controller 300 (FIG. 3A) supported within the handle assembly 20. The reload assembly 16 supports an annular staple cartridge 48 that includes a plurality of staples (not shown). The anvil assembly 50 includes an anvil head 28 that includes a staple forming surface 29 (FIG. 2A).

The handle assembly 20 is illustrated as a powered assembly and includes a stationary grip 22, an actuation button 24 for controlling firing of staples (not shown) from the staple cartridge 48 of the reload assembly 16, and approximation buttons 26a, 26b for controlling axial displacement of the anvil assembly 50 towards and away from the staple cartridge 48 of the reload assembly 16 between open and clamped positions. For a detailed description of the structure and function of exemplary powered handle assemblies, reference may be made to U.S. Patent Application Publication Nos. 2020/0015820 and 2019/0343517. Although the disclosure illustrates a powered assembly, it is envisioned that advantages of the disclosure, as described in detail below, are also applicable to robotically actuated surgical instruments and/or manually operated staplers (e.g., including a force sensor that provides an indication that the acceptable clamping force has been reached when manual approximation is being performed).

Figure 2A:
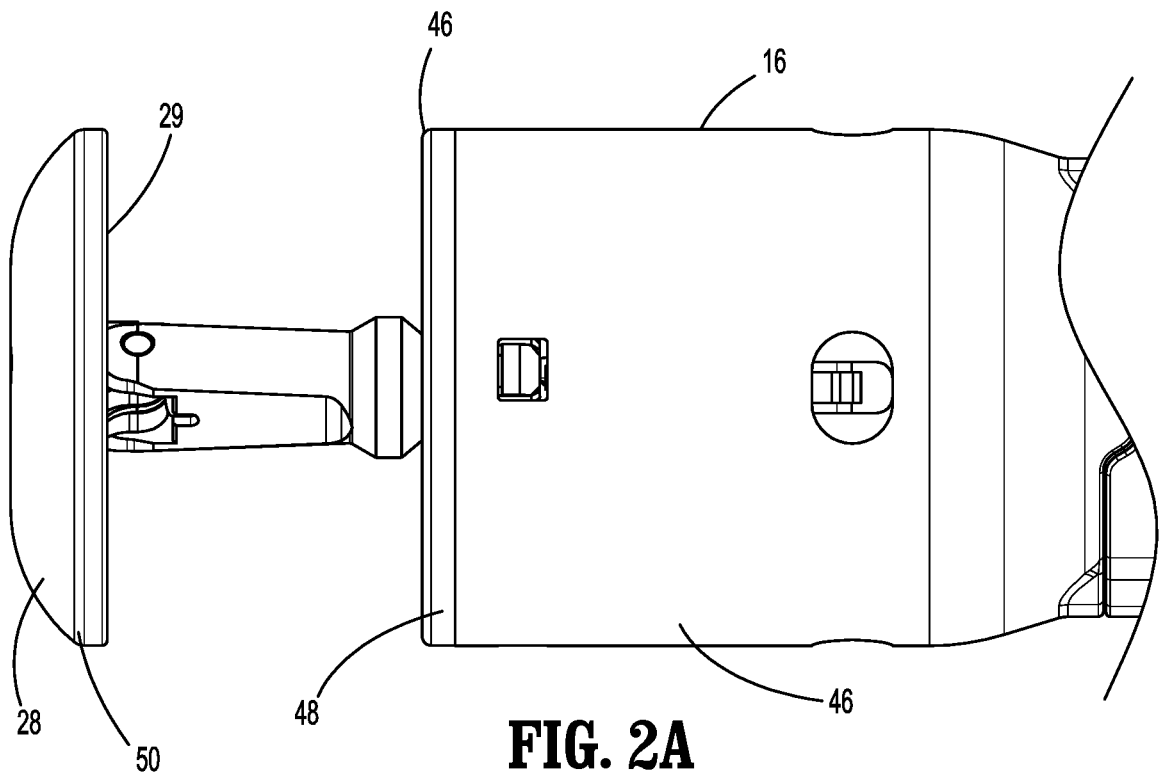
FIGS. 2A-2B are illustrations depicting the surgical stapling instrument of FIG. 1 in the open and clamped positions.
Figure 2B:
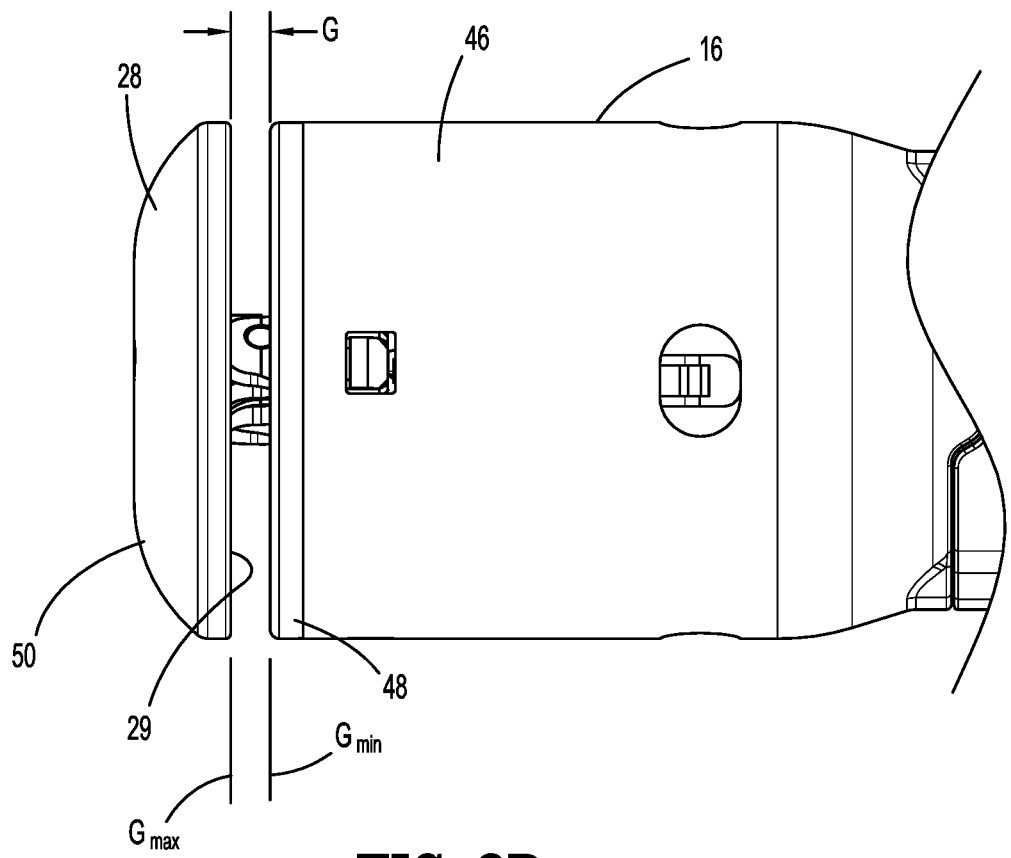

FIGS. 2A and 2B illustrate the surgical stapling instrument 10 in the open and clamped positions. In the open position (FIG. 2A), the anvil assembly 50 is spaced from the staple cartridge 48 of the reload assembly 16 to facilitate placement of tissue between the staple forming surface 29 of the anvil head 28 of the anvil assembly 50 and the staple cartridge 48 of the reload assembly 16. In the clamped position, the anvil assembly 50 is moved into juxtaposed alignment with the staple cartridge 48 to define a tissue gap "G" between the staple forming surface 29 of the anvil head 28 of the anvil assembly 50 and the staple cartridge 48 of the reload assembly 16. In current stapling instruments, both manual and powered, the stapling instruments include a lockout to prevent firing of the stapling instrument unless the tissue gap "G" is within a predetermined range. This predetermined range is determined based in part on the size of the staple being formed and ensures that the anvil head 28 of the anvil assembly 50 is in close enough proximity to the staple cartridge 48 to properly form staples. The predetermined tissue gap range is defined by a maximum acceptable to gap $G_{max}$ and a minimum acceptable tissue gap $G_{min}$.

The handle assembly 20 may include an electrical assembly such as a strain gauge 360 (FIG. 3A) that communicates with the controller 300 (FIG. 3A) and is configured to determine the load on a motor (not shown) of the surgical stapling instrument 10 resulting from tissue being clamped between the anvil assembly 50 and the staple cartridge 48. This determination can be used to determine a force of compression on the tissue that is clamped between the anvil assembly 50 and the staple cartridge 48.

With continued reference to FIG. 1, the adapter assembly 100 includes an interface portion 232 that is detachably coupled to the handle assembly 20, a tubular shaft 234 that extends distally from the interface portion 232, a drive coupling assembly (not shown) which is movably supported within the adapter assembly 100, and a drive shaft (not shown) that is coupled to an anvil shaft 52 of the anvil assembly 50. The drive coupling assembly (not shown) is engaged with and driven by the handle assembly 20 to control axial displacement of the drive shaft to move the anvil assembly 50 in relation to the staple cartridge 48 between the open and clamped positions.

The reload assembly 16 is supported on a distal portion of the adapter assembly 100 and includes a shell housing 46 that supports the staple cartridge 48. In aspects of the disclosure, the staple cartridge 48 defines annular rows of staple receiving pockets 48a (FIG. 1). In some aspects of the disclosure, the reload assembly 16 is releasably coupled to the distal portion of the adapter assembly 100 to facilitate the replacement of the annular staple cartridge 48 after each use.

Each of the staple receiving pockets 48a of the staple cartridge 48 supports a staple (not shown) that can be fired from the staple cartridge 48 via actuation of the actuation button 24 of the handle assembly 20. The shell housing 46 of the reload assembly 16 defines an annular cavity 60. The annular cavity 60 supports a staple pusher (not shown) and an annular knife (not shown) which are movable in relation to the staple cartridge 48 to eject the staples from the staple cartridge 48 and to dissect or cut tissue positioned within an annulus defined by the staple cartridge 48. When the staples (not shown) are fired from the staple cartridge 48, the staples are driven into and formed within the staple forming pockets of the staple forming surface 29 of the anvil head 28 of the anvil assembly 50.

Figure 3A:
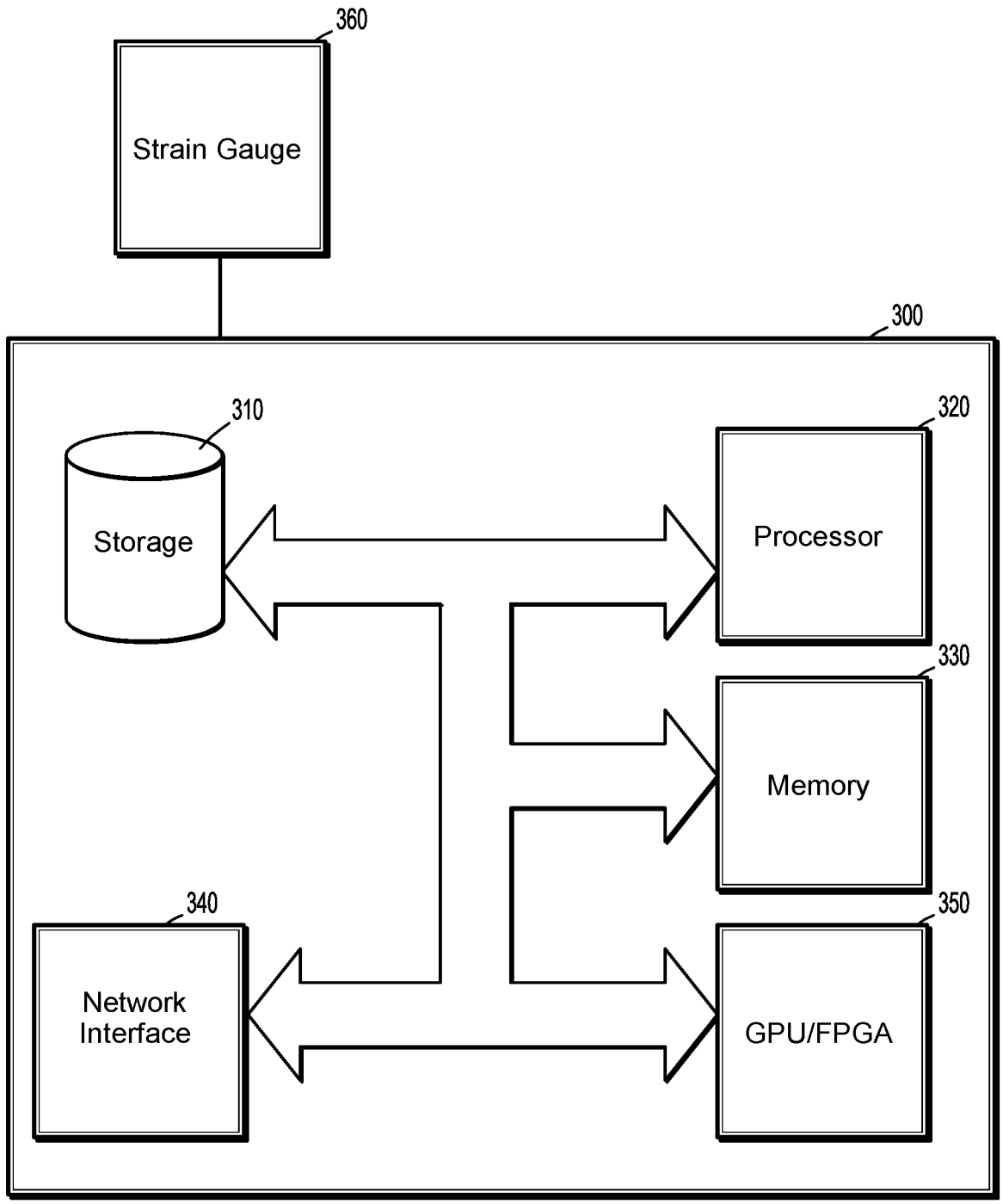
FIG. 3A is a block diagram of a controller provided in accordance with the disclosure and configured for use with the surgical system of FIG. 1.

FIG. 3A illustrates the controller 300, in accordance with the disclosure, which includes a processor 320 that is connected to a computer-readable storage medium or a memory 330. The computer-readable storage medium or memory 330 may be a volatile type memory, e.g., RAM, or a non-volatile type memory, e.g., flash media, disk media, etc. In various aspects of the disclosure, the processor 320 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memistors, chemically, or other inference calculations, as opposed to processors.

In aspects of the disclosure, the memory 330 can be random access memory, read-only memory, magnetic disk memory, solid-state memory, optical disc memory, and/or another type of memory. In some aspects of the disclosure, the memory 330 can be separate from the controller 300 and can communicate with the processor 320 through communication buses of a circuit board and/or through communication cables such as serial ATA cables or other types of cables. The memory 330 includes computer-readable instructions that are executable by the processor 320 to operate the controller 300. In other aspects of the disclosure, the controller 300 may include a network interface 340 to communicate with other computers or to a server. A storage device 310 may be used for storing data.

In aspects of the disclosure, the strain gauge 360 is coupled to the processor, and the disclosed method is run on the controller 300 or on a user device, including, for example, on a mobile device, an IoT device, or a server system.

Figure 3B:
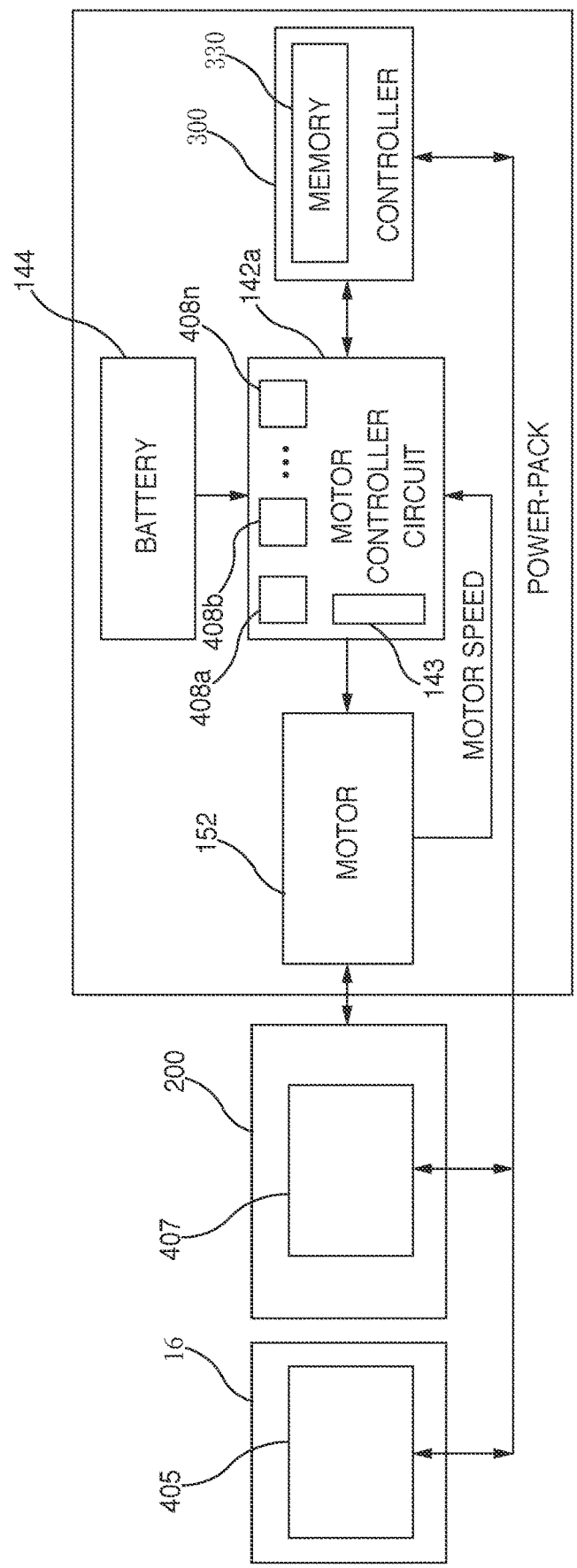
FIG. 3B is a block diagram of the handle assembly, the adapter assembly, and the reload assembly of the surgical system of FIG. 1 in accordance with the disclosure.

With reference to FIG. 3B, a schematic diagram of the handle assembly 20, the adapter assembly 200, and the reload assembly 16, is shown. For brevity, only one of the motors 152, 154, 156 are shown, namely, motor 152. The motor 152 is coupled to the battery 144. In aspects, the motor 152 may be coupled to any suitable power source configured to provide electrical energy to the motor 152, such as an AC/DC transformer.

The battery 144 and the motor 152 are coupled to the motor controller circuit board 142a having a motor controller 143, which controls the operation of the motor 152, including the flow of electrical energy from the battery 144 to the motor 152. The main controller circuit board 142b (FIG. 1) includes a main controller 300, which controls the handle assembly 20. The motor controller 143 includes a plurality of sensors 408a, 408b, . . . 408n configured to measure operational states of the motor 152 and the battery 144. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft 106, 108, 110 (FIG. 2A) coupled thereto and rotatable by the motor 152. Position of various axially movable drive shafts may also be determined by using various linear sensors disposed in or in proximity to the shafts or extrapolated from the RPM measurements. In aspects, torque may be calculated based on the regulated current draw of the motor 152 at a constant RPM. In further aspects, the motor controller 143 and/or the main controller 300 may measure time and process the above-described values as a function of time, including integration and/or differentiation, e.g., to determine the rate of change in the measured values. The main controller 300 is also configured to determine distance traveled of various components of the circular adapter assembly 200 and/or the reload assembly 16 by counting revolutions of the motors 152, 154, and 156.

The motor controller 143 is coupled to the main controller 300, which includes a plurality of inputs and outputs for interfacing with the motor controller 143. In particular, the main controller 300 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions, which are discussed in more detail below. The main controller 300 is also configured to accept a plurality of user inputs from a user interface (e.g., switches, buttons, touch screen, etc. coupled to the main controller 300).

The main controller 300 is also coupled to the strain gauge 360 of the circular adapter assembly 200 using a wired or a wireless connection and is configured to receive strain measurements from the strain gauge 360 which are used during operation of the handle assembly 20.

The reload assembly 16 includes a storage device 405 (e.g., chip 464c). The adapter assembly 200 also includes a storage device 407. The storage devices 405 and 407 include non-volatile storage medium (e.g., EEPROM) that is configured to store any data pertaining to the reload assembly 16 and the circular adapter assembly 200, respectively, including but not limited to, usage count, identification information, model number, serial number, staple size, stroke length, maximum actuation force, minimum actuation force, factory calibration data, and the like. In aspects, the data may be encrypted and is only decryptable by devices (e.g., main controller 300) have appropriate keys. The data may also be used by the main controller 300 to authenticate the circular adapter assembly 200 and/or the reload assembly 16. The storage devices 405 and 407 may be configured in read only or read/write modes, allowing the main controller 300 to read as well as write data onto the storage device 405 and 407.

When the surgical stapling instrument 10 is used to conduct a surgical procedure, the surgical stapling instrument 10 is manipulated to position tissue between the staple cartridge 48 and the anvil assembly 50. Once the surgical instrument is properly positioned in relation to the tissue to treat tissue, the handle assembly 20 is actuated to move the anvil assembly 50 towards the clamped position to the $G_{min}$ position.

Figure 4:
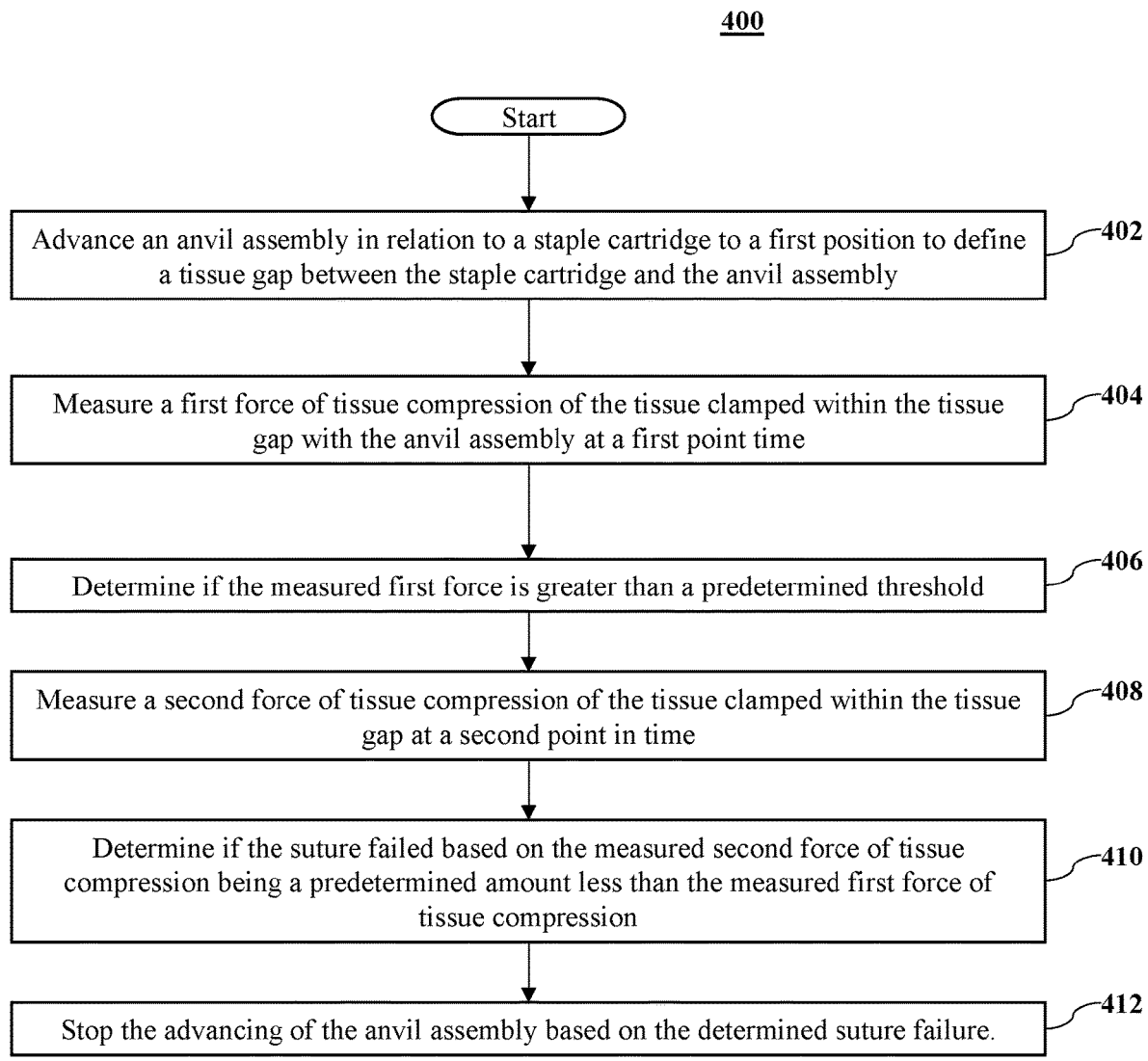
FIG. 4 is a flowchart of a method for controlling a surgical stapling instrument for stapling in accordance with the disclosure.
Figure 6:
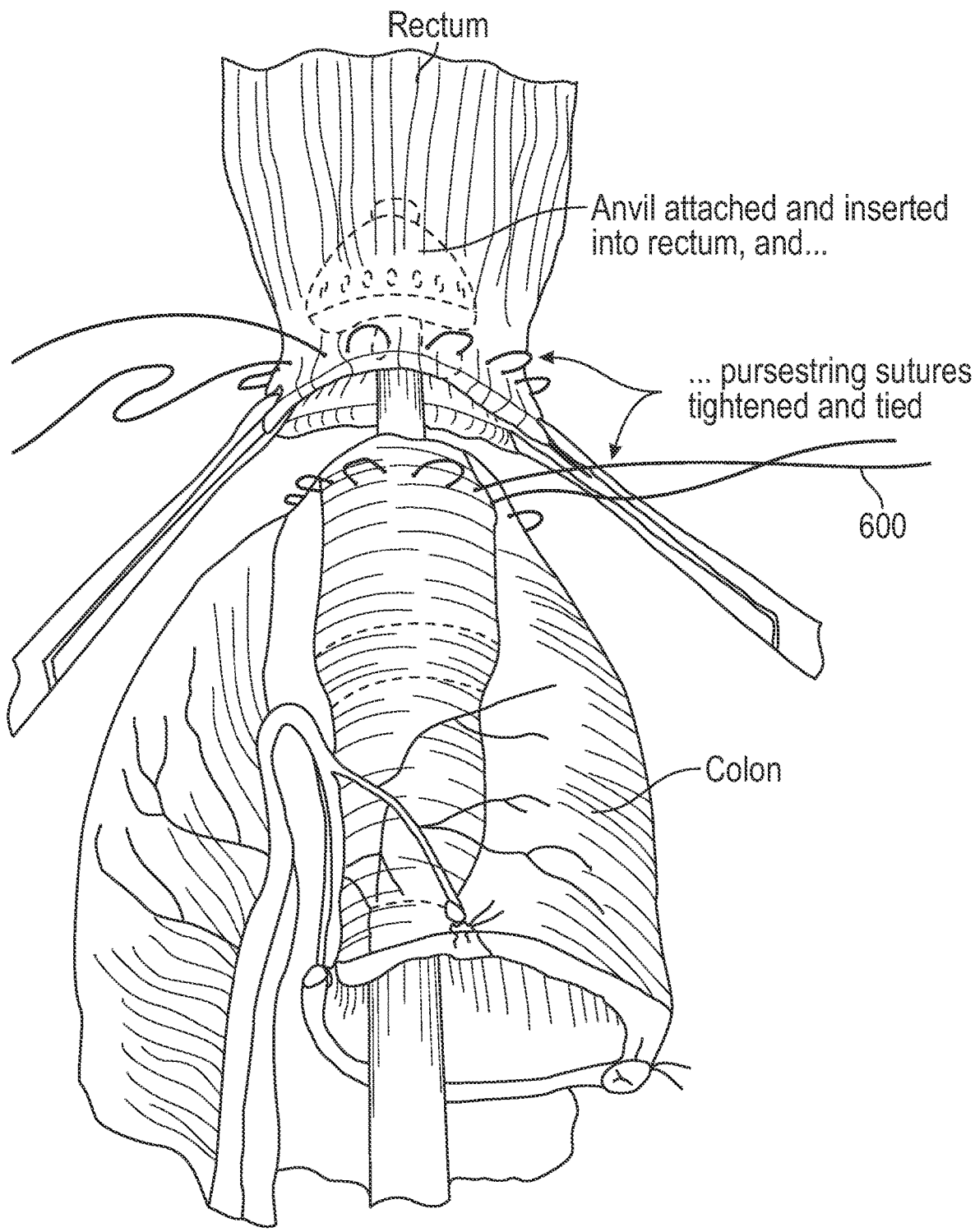
FIG. 6 is an illustration of a purse-string suture provided in accordance with the disclosure and configured for use with the surgical system of FIG. 1.

FIG. 4 illustrates a flow diagram of a computer-implemented method 400 for controlling a surgical stapling instrument and detecting a suture failure during the clamping of tissue. During a procedure, a purse-string suture 600 (FIG. 6) may be tied around one or both sides of the tissue covering the surgical stapling instrument in order to enhance the integrity of the anastomosis and help prevent leakage. During a first clamping phase, the anvil assembly 50 (FIG. 1) is moved in relation to the staple cartridge 48 from an open position to a clamped position in which a tissue gap defined between the anvil assembly 50 and the staple cartridge 48 is within a predetermined acceptable gap range to facilitate proper staple formation. More specifically, in the first clamping phase, the anvil assembly 50 is approximated in relation to the staple cartridge 48 of the reload assembly 16 to define the tissue gap of $G_{max}$ (Step 402). In aspects of the disclosure, $G_{max}$ may be from about 0.037 inches to about 0.024 inches. However, the value of $G_{max}$ may vary depending on the size of the staples within the staple cartridge 48. The clamped tissue includes a suture.

Once the anvil assembly 50 is moved in relation to the staple cartridge 48 until the tissue gap of $G_{max}$ is reached, a force of tissue compression on the tissue clamped between the staple cartridge 48 and the anvil assembly 50 is measured (Step 404) at a first point in time. As discussed above, the clamping force of the tissue clamped between the anvil assembly 50 and the staple cartridge 48 of the shell assembly can be measured using a strain gauge 360 that communicates with the controller 300. Alternatively, any other force or strain measuring device may be used to measure the clamping force of the tissue clamped between the anvil assembly 50 and the staple cartridge 48. For example, the current draw on a motor 154 in the handle assembly 20 that drives a drive shaft 106 (FIG. 2A) may be used to measure the clamping force. If the compression force on the tissue being greater than a predetermined threshold (Step 406), the surgical stapling instrument 10 continues to advance the anvil assembly 50 in relation to the staple cartridge 48. The predetermined threshold may vary based on the type and thickness of the tissue being compressed and may be set automatically by the instrument 10 or by the user.

The force of tissue compression on the tissue clamped between the staple cartridge 48 and the anvil assembly 50 is measured (Step 408) at a second point in time. If the compression force at the second point in time is less than the compression force at the first point in time, the controller determines that the purse-string suture has failed (Step 410). Purse-string suture failure may include a non-limiting list of, for example, a ruptured suture, failure of the suture material, and/or a suture that has detached from tissue. The compression force at the second point in time may have a sharp decrease from the compression force at the first point in time (see, e.g., FIG. 5 curve 502), which is indicative of purse-string suture failure.

Figure 5:
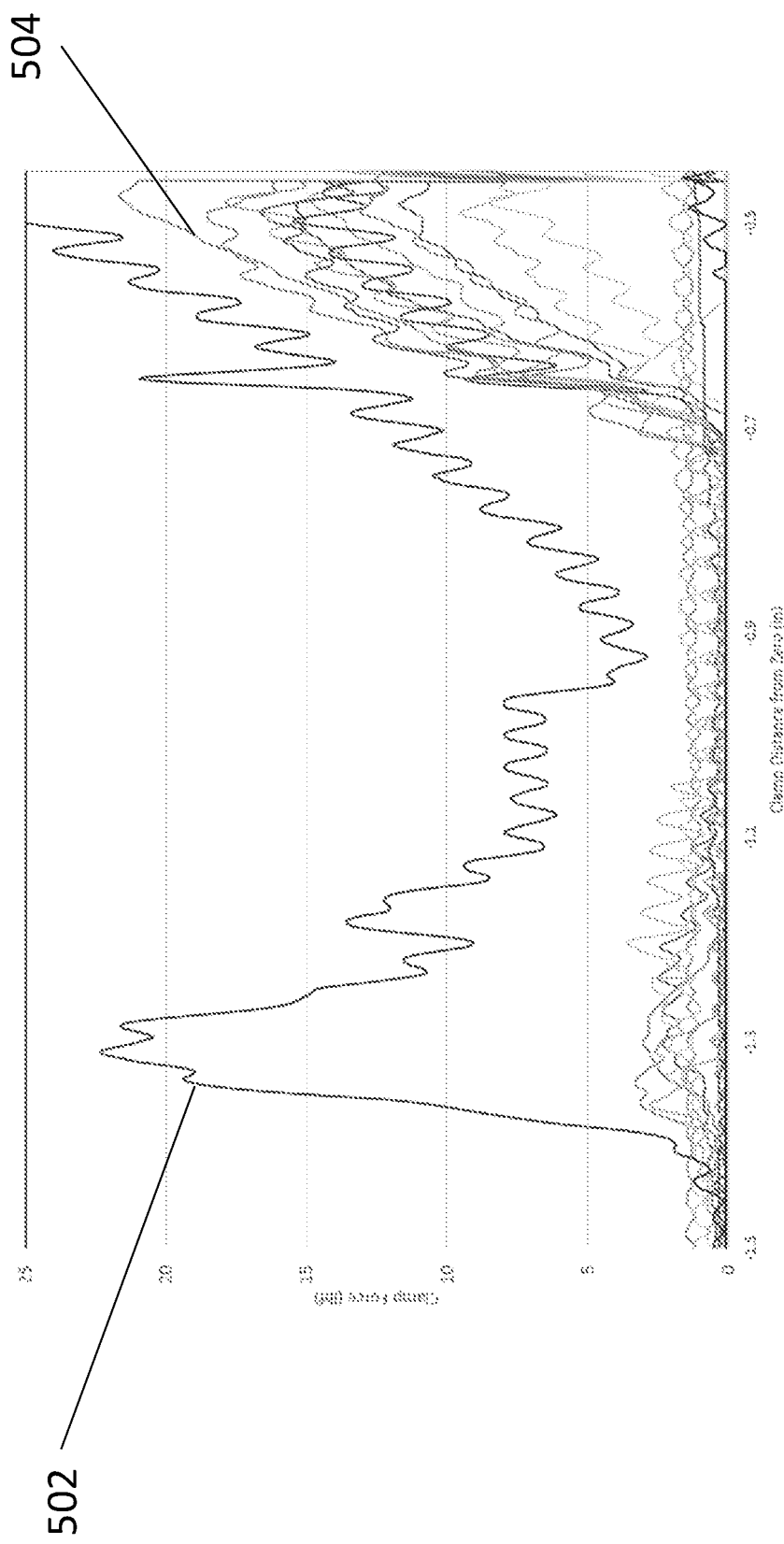
FIG. 5 is a graph illustrating strain gauge profiles during clamping of tissue in accordance with the disclosure.

FIG. 5 is a graph illustrating strain gauge profiles during clamping of tissue. For example, these forces may be seen when the anvil assembly 50 is about 1.500" to about 0.460" from the staple cartridge 48. Curve 502 represents clamped tissue that triggered an obstruction force limit error due to the force seen by a purse-string suture failing during clamp. All other curves 504 show normal clamped tissue, without incident. These curves represent five different procedure types in the colorectal space.

In various aspects, the compression force may be monitored over time, e.g., as a curve. In various aspects, the controller 300 may analyze the shape of the curve, including rate of change, shape, etc., and compare the curve to a stored database of curves, and determine suture failure based on the difference between properties of the measured curve and the stored curves. In various aspects, the controller may use measured compression force values that are measured when the anvil assembly 50 is within a first predetermined range of the staple cartridge 48 and not in a second predetermined range a predetermined range relative to the staple cartridge 48. For example, the first predetermined range may be when the anvil assembly 50 is about 1.500" to about 0.9" from the staple cartridge 48, for example, a range of distances where the tissue compression force normally would be below a threshold value indicating that tissue is not being compressed, and the second predetermined range may be when the anvil assembly 50 is about 0.7" to about 0.45" from the staple cartridge 48, for example, a range of distances where the tissue compression force would normally be above a threshold value indicating that tissue is being compressed.

If the controller has determined that the suture has failed, the surgical stapling instrument 10 does not enter the firing mode. As such, the surgical stapling instrument 10 is prevented from entering the firing mode and, the controller # may provide a warning on a display 146 (FIG. 1) on, e.g., the handle assembly of the surgical stapling instrument, to alert the surgeon that compression force is too high, and to stop clamping the tissue, such that the surgeon can reposition the surgical stapling instrument 10 on the tissue and replace the suture. In some aspects, the warning may alert the surgeon to inspect the surgical site. In various aspects, the surgical stapling instrument 10 may generate an audible warning such as a beep, a tone, or a spoken phrase. For example, the spoken phrase may alert the surgeon to inspect the surgical site for a failed suture.

Although this disclosure is directed to a powered surgical stapling instrument, it is envisioned the principles of this disclosure are applicable to manually powered stapling instruments. For example, the clamping force on tissue clamped between an anvil assembly and a staple cartridge of the stapling instrument can be measured as the stapling instrument is moved through a predetermined acceptable tissue gap range. In such a device, an indicator such as a light can be provided on the instrument. When the clamping force of the tissue enters the predetermined acceptable range of compression with the instrument within the predetermined acceptable gap range, the indicator can be activated to notify the surgeon that the instrument is ready to be fired.

It is envisioned that the aspects of this disclosure, although illustrated in association with a circular stapling instrument, are equally applicable to other types of stapling instruments, including linear stapling devices, vessel sealing devices, and other devices for joining tissue sections together.

Persons skilled in the art will appreciate that one or more operations of the method 500 may be performed in a different order, repeated, and/or omitted without departing from the scope of the disclosure. In various aspects, the illustrated method 500 can operate in the controller 300 (FIG. 3A), in a remote device, or in another server or system. Other variations are contemplated to be within the scope of the disclosure. The operations of method 500 will be described with respect to a controller, e.g., controller 300 (FIG. 3A) of surgical stapling instrument 10 (FIG. 3A), but it will be understood that the illustrated operations are applicable to other systems and components thereof as well.

Persons skilled in the art will understand that the instruments and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical stapling instrument comprising:
    an anvil assembly including an anvil head and an anvil center rod extending proximally from the anvil head;
    a reload assembly including an annular staple cartridge including a plurality of staples;
    a processor; and
    a memory, including instructions stored thereon, which when executed by the processor, cause the surgical stapling instrument to:
        advance the anvil assembly in relation to the staple cartridge to a first position defining a tissue gap between the staple cartridge and the anvil assembly and clamping tissue therebetween, the clamped tissue including a suture therethrough;
        measure a force of tissue compression of the tissue clamped within the tissue gap over a period of time;
        determine whether a suture failure has occurred based on a shape of a curve of the measured force over the period of time; and
        stop the advancing of the anvil assembly based on the determination of a suture failure.

2. The surgical stapling instrument according to claim 1, wherein the force of tissue compression is measured by a strain gauge.

3. The surgical stapling instrument according to claim 1, wherein the shape of the curve indicates a type of surgical procedure.

4. The surgical stapling instrument according to claim 1, wherein the instructions, when executed by the processor, further cause the surgical stapling instrument to prevent staple firing when the measured force of tissue compression increases over time over a predetermined threshold.

5. The surgical stapling instrument according to claim 4, wherein the predetermined threshold is greater than a predetermined acceptable range of tissue compression.

6. The surgical stapling instrument according to claim 1, wherein the instructions, when executed by the processor, further cause the surgical stapling instrument to generate a warning in response to the determination of a suture failure.

7. The surgical stapling instrument according to claim 6, wherein the warning includes at least one of a warning to inspect a surgical site or a warning to unclamp the tissue.

8. The surgical stapling instrument according to claim 1, wherein the instructions, when executed by the processor, further cause the surgical stapling instrument to generate an audio warning when suture failure is determined.

9. The surgical stapling instrument according to claim 1, wherein the instructions, when executed by the processor, further cause the surgical stapling instrument to determine a decrease in tissue clamping force over the period of time based on the shape of the curve.

10. A computer-implemented method for controlling a surgical stapling instrument, comprising:
    advancing an anvil assembly in relation to a staple cartridge to a first position defining a tissue gap between the staple cartridge and the anvil assembly and clamping tissue therebetween, the clamped tissue including a suture therethrough;
    measuring a force of tissue compression of the tissue clamped within the tissue gap over a period of time;
    determining whether a suture failure has occurred based on a shape of a curve of the measured force over the period of time; and
    stopping the advancing of the anvil assembly based on the determination of a suture failure.

11. The computer-implemented method of claim 10, wherein the force of tissue compression is measured by a strain gauge.

12. The computer-implemented method of claim 10, wherein the shape of the curve indicates a type of surgical procedure.

13. The computer-implemented method of claim 10, further comprising preventing staple firing when the measured force of tissue compression increases over time over a predetermined threshold.

14. The computer-implemented method of claim 13, wherein the predetermined threshold is greater than a predetermined acceptable range of tissue compression.

15. The computer-implemented method of claim 10, further comprising displaying a warning in response to the suture failure being determined.

16. The computer-implemented method of claim 15, wherein the displayed warning includes at least one of a warning to inspect a surgical site or a warning to unclamp the tissue.

17. The computer-implemented method of claim 10, further comprising generating an audio warning when suture failure is determined.

18. The computer-implemented method of claim 10, further comprising determining a decrease in tissue clamping force the period of time based on the shape of the curve.

19. The computer-implemented method of claim 10, wherein measuring a first force of tissue compression of the tissue clamped within the tissue gap at a first time point includes measuring the first force of tissue compression when the anvil assembly is not within a predetermined distance range of the staple cartridge.

20. A non-transitory computer-readable medium storing instructions which, when executed by a processor, cause the processor to perform a method for controlling a surgical stapling instrument, comprising:

advancing an anvil assembly in relation to a staple cartridge to a first position defining a tissue gap between the staple cartridge and the anvil assembly and clamping tissue therebetween, the clamped tissue including a suture therethrough;

measuring a force of tissue compression of the tissue clamped within the tissue gap over a period of time;

determining whether the suture failed based on a shape of a curve of the measured force over the period of time; and stopping the advancing of the anvil assembly based on the determination of a suture failure.

\* \* \* \* \*